United States Patent [19]
Jackson et al.

[11] Patent Number: 5,350,370
[45] Date of Patent: Sep. 27, 1994

[54] HIGH WICKING LIQUID ABSORBENT COMPOSITE

[75] Inventors: David M. Jackson, Roswell; Billie J. Matthews, Woodstock, both of Ga.

[73] Assignee: Kimberly-Clark Corporation, Neenah, Wis.

[21] Appl. No.: 56,280

[22] Filed: Apr. 30, 1993

[51] Int. Cl.⁵ .................... A61F 13/15; A61F 13/20
[52] U.S. Cl. ..................... 604/367; 604/358; 604/365; 604/366; 604/368; 604/370; 604/374; 604/385.1
[58] Field of Search ............... 604/358, 368, 374–380, 604/382, 384, 365–367, 370, 385.1; 602/45

[56] References Cited

U.S. PATENT DOCUMENTS

| | | |
|---|---|---|
| 3,971,373 | 7/1976 | Braun . |
| 4,100,324 | 7/1978 | Anderson . |
| 4,118,531 | 10/1978 | Hauser . |
| 4,429,001 | 1/1984 | Kolpin et al. . |
| 4,500,315 | 2/1985 | Pieniak et al. . |
| 4,537,590 | 8/1985 | Pieniak et al. . |
| 4,540,454 | 9/1985 | Pieniak et al. . |
| 4,559,050 | 12/1985 | Iskra . |
| 4,585,448 | 4/1986 | Enloe . |
| 4,604,313 | 8/1986 | McFarland et al. . |
| 4,605,402 | 8/1986 | Iskra . |
| 4,650,479 | 3/1987 | Insley . |
| 4,655,757 | 4/1987 | McFarland et al. . |
| 4,673,402 | 6/1987 | Weisman et al. . |
| 4,685,915 | 8/1987 | Hasse et al. . |
| 4,699,823 | 10/1987 | Kellenberger ............... 604/378 |
| 4,724,114 | 2/1988 | McFarland et al. . |
| 4,773,903 | 9/1988 | Weisman et al. . |
| 4,865,596 | 9/1989 | Weisman et al. . |
| 4,888,231 | 12/1989 | Angstadt . |
| 4,902,559 | 2/1990 | Eschwey et al. . |
| 4,923,454 | 5/1990 | Seymour et al. . |
| 4,935,022 | 6/1990 | Lash et al. . |
| 5,188,624 | 2/1993 | Young, Sr. et al. ............... 604/368 |

FOREIGN PATENT DOCUMENTS

| | | |
|---|---|---|
| 0254476 | 1/1988 | European Pat. Off. . |
| 0325416 | 7/1989 | European Pat. Off. . |
| 0339461 | 11/1989 | European Pat. Off. . |
| 2112828 | 7/1983 | United Kingdom . |
| 2113731 | 8/1983 | United Kingdom . |
| 2151272 | 7/1985 | United Kingdom . |
| 2208804 | 4/1989 | United Kingdom . |

Primary Examiner—Randall L. Green
Assistant Examiner—P. Zuttarelli
Attorney, Agent, or Firm—Patrick C. Wilson

[57] ABSTRACT

Disclosed herein is a high wicking liquid absorbent composite suitable for a wide number of uses including personal care products and the process for making the same. The composite is made from a relatively uniform mixture of from about 5 to about 20 percent fine wettable fiber, from about 3 to about 30 percent pulp fibers, from about 50 to about 90 percent superabsorbent and from 0 to about 10 percent binder, the percentages being on a dry weight basis. The mixture is compressed into a composite having a density of from about 0.1 to about 0.5 grams per cubic centimeter and a vertical wicking height of at least about 10 centimeters in one hour. The process involves forming a sheet comprising 50 to 90 percent fine wettable fiber and 10 to 50 percent pulp fiber on a dry weight basis. The sheet is then fiberized into a plurality of individual fibers within an air stream. A superabsorbent is then mixed with the fibers from the fiberized sheet in the air stream to form a uniform mixture and the uniform mixture is deposited onto a forming surface to form a composite. After forming the composite, it is compressed to a desired density.

15 Claims, 2 Drawing Sheets

HIGH WICKING LIQUID ABSORBENT COMPOSITE

BACKGROUND OF THE INVENTION

The present invention relates to a high superabsorbent content fluff/wood pulp absorbent. More particularly, the present invention relates to a high superabsorbent containing absorbent which has increased wicking ability.

Perhaps the oldest known liquid absorbents to man are those products made from cotton, wood pulp or fluff and other natural materials. These materials have been used routinely to absorb liquids, and in particular, body fluids, in connection with personal care and other absorbent articles such as diapers, training pants, incontinence garments, sanitary napkins, bandages, and the like. As the development of these products has progressed, so too has the need for increased liquid retention capacity. One means for increasing the liquid retention capabilities of such products is through the addition of superabsorbents which are also referred to as hydrogels and hydrocolloids. This is particularly true in the case of diapers, training pants and incontinence garments. As these products have become more and more sophisticated, the manufacturers of these products have reduced the amount of wood pulp or fluff in the absorbent layers of these materials and replaced the fluff with varying amounts of superabsorbent.

As the amount of superabsorbent has increased in these absorbent structures, a problem called gel-blocking has arisen. Early superabsorbents were made in particle form and while being capable of absorbing many times their own weight in liquid such as water and urine, would not hold their particle or generally spherical shape as they absorbed liquid. Instead, they would turn into a mushy gel which would swell, fill the voids between the wood pulp fibers and quickly turned the structure into a gelled mess. This is now referred to as gel blocking. As a result of this gel blocking, there were no longer any pores or capillaries through which to transport additional quantities of liquid. Consequently, using diapers as an example, despite the overall high liquid retention capability of the absorbent, very little of the liquid-absorbing capacity could be utilized because of the gel-blocking problem. After a first or second insult, the area receiving the liquid would gel block, the liquid would not absorb and sometimes run off the surface of the gel mass and would even leak out of the diaper. Because of this, there was only a finite amount of superabsorbent which could be added to the absorbent structure.

As superabsorbent work developed, superabsorbent particles were created which had a high liquid capacity and a higher gel strength in the sense that the particles would absorb greater amounts of liquid and still retain their generally spherical shape. As a result, the amount of superabsorbent which could be added to the absorbent portion of a personal care absorbent product, such as a diaper, increased. Manufacturers could, therefore, remove more wood pulp and replace it with superabsorbent. In addition, the manufacturers found that they could more highly compress the absorbent to create a much thinner diaper. Here again, however, a problem arose with the ability of the absorbent in the diaper to utilize its entire capacity.

With the new high gel strength, higher capacity superabsorbents the problem with gel blocking decreased, but a new problem took its place. As the new superabsorbents swelled upon absorbing liquid, their diameters would greatly increase. Highly compressing the fluff/superabsorbent composite absorbents helped to maintain the liquid-transporting properties of the absorbent, but there was still a problem with the full utilization of the absorbent's capacity. This was because as the superabsorbent particles swelled, they pushed the absorbent structure open and apart. On a microscopic scale, this expansion created large voids within the absorbent structure, thereby greatly reducing the capillary action within the absorbent and thus the ability of the absorbent to transport and wick liquids away from the insult zone to other areas of the absorbent composite in the diaper so that the capacity of the diaper could be more fully utilized. In essence, the liquid transport/wicking problem went from an absorbent which gel blocked and had virtually no capillaries to transport liquid to an absorbent which became too open and, therefore, did not have sufficient capillary action to wick and transport the liquids away from the insult zone. As a result, there again became an upper limit as to the amount of superabsorbent which could be added to a fluff-based absorbent. This problem was exacerbated by the fact that existing pulp does not have sufficient surface area per unit mass to compensate for the disruptions in the capillarity due to the swelling of the superabsorbent particles.

It is, therefore, an object of the present invention to provide an absorbent structure which can utilize wood pulp with a high loading of superabsorbent.

It is another object of the present invention to create a wood pulp/superabsorbent composite which has increased capillarity and wicking action thereby making an absorbent structure which can more efficiently utilize its liquid-retentive capabilities. These and other objects of the present invention will become more apparent on a further review of the following specification and claims.

SUMMARY OF THE INVENTION

The present invention is directed to a high wicking liquid absorbent composite and the process for making the same as well as several resultant products. The process involves forming a slurry of fine wettable fibers and pulp fibers in a solvent such as water with the slurry having a solids content by weight of from between about 1 and about 5 percent based upon the total weight of the slurry. The solids content and the slurry is made up of from about 10 to about 50 percent pulp fiber and from about 50 to about 90 percent fine wettable fiber on a dry weight basis. Next a sheet is formed from the slurry on a foraminous forming surface with the sheet having a weight of from about 350 to about 720 grams per square meter and a moisture content of between about 6 and about 15 percent.

Once the sheet has been formed, it is then fiberized into a plurality of fibers within an air stream and mixed with a superabsorbent and optionally a binder to form a mixture within the air stream. The entrained materials are then deposited onto a forming surface to form a composite with a basis weight ranging from about 100 to about 1000 grams per square meter. The composite is then compressed to a density of about 0.1 to about 0.5 grams per cubic centimeter.

The high wicking liquid absorbent composite once formed will have a relatively uniform mixture of from about 5 to about 20 percent fine wettable fiber, from about 3 to about 30 percent pulp fibers, from about 50 to about 90 percent superabsorbent and from about 0 to about 10 percent binder with the percentages being on a dry weight basis.

Due to the improved wicking ability of the present invention, the composite material is very well suited as an absorbent material for a wide variety of uses not the least of which is personal care absorbent products. Examples of such products include diapers, training pants, incontinence garments, sanitary napkins, bandages and the like. In addition, if desired, the composite can be formed with specific zones containing greater or lesser amounts of fine wettable fiber to tailor the particular absorbent composite to a specific need.

DETAILED DESCRIPTION OF THE INVENTION

Figure 1:
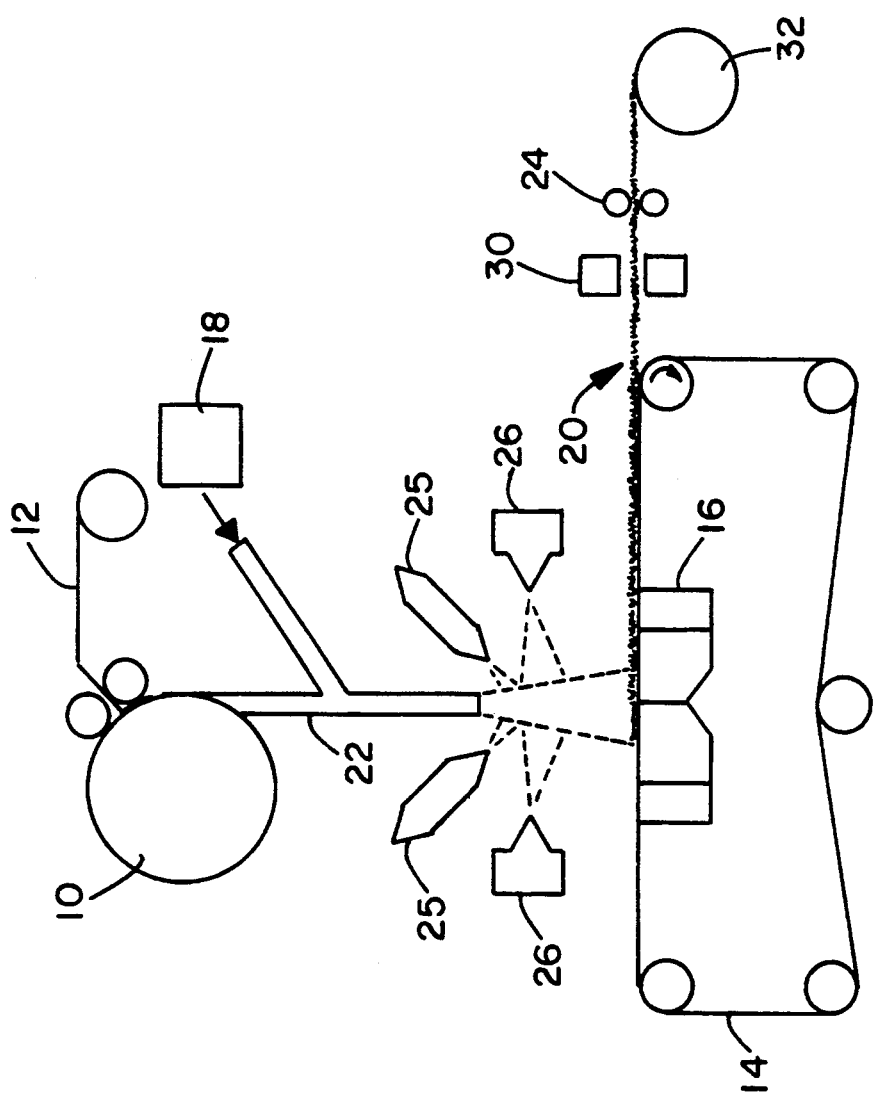
FIG. 1 is a schematic view of a process for forming a high wicking liquid absorbent composite according to the present invention.

The present invention is directed to a high wicking absorbent composite material containing a conventional absorbent such as wood pulp(fluff) and a high concentration of superabsorbent. Unlike prior materials which tended to gel block or resist wicking of retained liquids, the material of the present invention has increased wicking ability due to the addition of a fine wettable fiber to the superabsorbent/wood pulp combination. While not intending to limit the scope of the present invention, the material of the present invention has particular use as an absorbent in diapers, training pants, incontinence garments, feminine hygiene products, bandages and the like. These products typically have an absorbent core which extends throughout the entire product. To increase the capacity of these products, high liquid retention materials called "superabsorbents", "hydrogels" or "hydrocolloids" have been added to the absorbent core to increase the liquid handling and retention capabilities of the absorbent core. Unfortunately, due to a number of factors, the superabsorbent/wood pulp absorbent core is not fully utilized. One reason is because of the inability of the absorbent core to wick the liquid away from the area of liquid entry or insult. Consequently, such products must be made with larger amounts of absorbent material than is actually necessary thereby increasing the thickness and overall cost of the products. The material of the present invention has helped reduce this problem by properly proportioning the components of the absorbent core and by adding what is termed a "fine wettable fiber" to increase the functional utilization of the absorbent core.

One indication of the relative efficiency of such absorbent cores is the measurement of the vertical wicking ability or height of the material. As will be shown in greater detail below, the material of the present invention has shown a marked increase in vertical wicking of liquids when compared to conventional superabsorbent/wood pulp absorbent cores. As a result, taking a diaper as an example, more of the absorbent core in the areas of the diaper worn away from the perineal area can be utilized to retain liquids, thereby allowing a greater reduction in the overall amount of absorbent core material used in the specific diaper construction. While the present invention will be described primarily in conjunction with its use in personal care products such as diapers, this is not intended to limit the scope of the present invention.

The high wicking liquid absorbent composite material of the present invention contains three main components and optionally a series of additional additives or components which can be used to enhance the properties of the absorbent composite material. The three main components include an absorbent support material, a superabsorbent and a fine wettable fiber the relative proportions of which will be described in further detail below. These three components are intimately mixed with one another, laid down on a forming surface and then compressed to a desired density to yield a composite with improved wicking characteristics.

The absorbent support material will most typically be a wood pulp or cellulose material such as wood pulp fibers (commonly referred to as fluff), cotton, cotton linters, bagasse or rayon fibers. In addition, synthetic counterparts to the foregoing materials are also considered to be within the scope of the present invention. Such absorbent support materials are typically in fiber form, generally with fiber lengths in the range of about to 2 to about 10 millimeters and with liquid retention capacities of about 8 grams per gram of material under a load of 0.5 pounds per square inch (3500 pascals) using 0.9% by weight saline solution. Examples of wood pulp fluff include CR2054 fluffing pulp produced by Kimberly-Clark Corporation of Neenab, Wis. and NB416 fluffing pulp produced by Weyerhauser Corporation of Federal Way, Washington.

The second component of the high wicking liquid absorbent composite material of the present invention is a superabsorbent material which is oftentimes referred to as a "hydrogel" or "hydrocolloid". Such superabsorbents are well known and produced in at least three forms including granules, fibers and flakes. Granular forms are the most common and typically have particle diameters in the range of about 50 to 1000 micrometers with liquid retention capacities in the range of 10 to 40 grams per gram of superabsorbent under a load of 0.5 pounds per square inch (3500 pascals) using 0.9% by weight saline solution. Such materials occur naturally and may also be synthesized. Examples of natural superabsorbents or hydrocolloids include gum arabic, agar, guar gum, starches, dextran and gelatin. Semi-synthetic versions include modified celluloses such as carboxymethyl cellulose and modified starches. Examples of synthetic absorbent gelling material polymers include but are not limited to polyvinylpyrrolidone and polyacrylates. Commercially available products include, but are not limited to, Hoechst-Celanese SANWET® IM5000 and IM3900 from Hoechst-Celanese Corporation of Charlotte, N.C.; Dow Drytech® 534 from Dow Chemical Company of Midland, Mich. and Allied Colloids SALSORB® 89 from Allied Colloids, Ltd. of Bradford, UK.

Fibrous superabsorbents are also commercially available. Typically these fibers will have diameters ranging from about 10 to 50 microns and lengths ranging from about 3 to 60 millimeters. Their absorbency will typically range between about 10 and about 40 grams per gram of superabsorbent under a load of 0.5 pounds per square inch (3500 pascals) using 0.9% by weight saline solution. Commercially available superabsorbent fibers include Allied Colloids/Courtalds FSA ® 101 and 111; ARCO FIBERSORB ® from Arco Corporation of Philadelphia, Pa.; and TOYO BOSEKI KK Lanseal from Toyo Boseki KK of Osaka, Japan.

The third component of the high wicking liquid absorbent composite of the present invention is a fine wettable fiber. This fine wettable fiber is a fiber which is very small in diameter in comparison to the fibers found in the conventional fluff-based absorbent core materials and the superabsorbent fibers defined above. Typically, the fine wettable fiber will have a length less than about 2 millimeters and a fiber diameter less than about 5 microns and generally the diameter will be between about 0.5 and 2.0 microns. The specific external surface areas of such fine wettable fibers will typically be in excess of about 2 square meters per gram of fiber and generally greater than 5 square meters per gram of fiber. The fiber should either have inherent hydrophilic properties or be treated so as to have such properties. As a result, the fine wettable fiber will have an advancing contact angle less than 90° and generally less than 70° using deionized water. Hoechst Celanese cellulose acetate Fibrets ® fibers from Hoechst Celanese Corporation of Charlotte, N. C. is an example of such fine wettable fibers. The Hoechst Celanese Fibrets ® fibers are highly fibrillated microfibers and have lengths ranging from between 20 and 200 microns and diameters of 0.5 to 5 microns with a total specific surface area of 20 square meters per gram, a specific gravity of 1.32, a softening temperature of between 360° and 400° F. and a melting temperature of 500° F. Another fine wettable fiber is the CFF ® fibrillated fiber from American Cyanamid Company of Stanford, Conn. This is an acrylic-based fiber with properties similar to the foregoing fibers.

The fine wettable fibers of the present invention prove particularly advantageous when used in conjunction with high swell superabsorbents. Certain superabsorbents when absorbing liquids swell more than others. When such high swell superabsorbents are used in absorbent composites, they will tend to expand. As they do, the center to center spacing between the particles increases thus increasing the void volume of the total composite. If the spacing becomes too large and thus the void volume becomes too great, then the capillarity of the structure will decrease, and, as a result, the absorbent composite cannot be fully utilized. The fine wettable fibers, however, will tend to bridge the gaps between the particles and provide a path for liquid transport. Consequently, the capillarity is maintained and the liquid can be wicked to more remote areas of the absorbent.

Testing has indicated that the foregoing three components should be uniformly mixed with one another to maximize the wicking and liquid storage capacity of the composite. In general, the composite will include a relatively uniform mixture of between about 5 and about 20% fine wettable fiber, between about 3 and about 30% pulp fiber or other absorbent support material and between about 50 and about 90% superabsorbent with the percentages being on a dry weight basis. The composite once formed is compressed so as to have a density ranging between about 0.1 and about 0.5 grams per cubic centimeter and once formed has a vertical wicking height of at least about 10 centimeters in one hour according to the test method described below.

In addition to the three main components, other components may be added to alter the overall properties of the liquid absorbent composite of the present invention. Examples of such additives include, but are not limited to, binders, wetting agents and anti-stats.

Binders serve to hold together the components of the present invention through mechanical entanglement, adhesion or both. The binder fibers can be relatively short staple fibers or more continuous fibers such as meltblown and spunbond fibers. Staple length fibers range in size from about 6 to 40 mm with denier sizes ranging from about 1.5 to 6 denier. Examples of staple fibers include straight or crimped single polymer staple fibers made from polyolefins, nylons or polyesters. Fusible synthetic pulps, such as PLEXAFIL ® from E. I. du Pont de Nemours of Wilmington, Del., may also be used for bonding purposes but typically have fiber sizes outside the aforementioned range. Multiconstituent fibers such as bicomponent fibers also may be used. Such bicomponent fibers can provide both mechanical and adhesive bonding when heated to bond their sheaths to surrounding materials.

In addition to binder fibers, adhesive sprays and powders may be used to bind the materials of the present invention. Spray adhesives are typically solvent-based and may be completely dissolved or emulsions. Powdered adhesives are usually heat activated. Water-based adhesives also may be used. Typically, the high wicking liquid absorbent composite of the present invention will have from 0 to about 10 percent binder on a dry weight basis.

Wetting agents may be added to the material of the present invention to increase wettability and liquid penetration. Examples of such wetting agents include Triton ® types X and N from Rohm and Haas Company of Philadelphia, Pa.; Igepal ® CO from GAF Corporation of Wayne, N.J.; Tergitol ® types from Union Carbide Corporation of Danbury, Conn. and Aerosol types from American Cyanamide of Stanford, Conn.

Anti-stats may be used to prevent fibers from clinging to equipment during web formation. Examples of anti-stats are well known to those of ordinary skill in the art.

Formation of the high wicking liquid absorbent composite of the present invention is dependent upon good mixing of the fine wettable fiber and the superabsorbent so that as the superabsorbent swells, the fine wettable fiber can act as the transport mechanism to move liquid away from the initial insult zone. Given the small size of the fine wettable fibers, it has been found that the handling and processing of these fibers can be difficult. As purchased, some of the fine wettable fibers come in the form of wet bricks or bales with a high solvent content, usually water, (15–30% solids) which must be broken up before further processing can take place. As a result, it has been found that the fine wettable fibers are easier to process if they are first mixed with standard wood pulp fibers, formed into a board and then refiberized before being mixed with the superabsorbent to form the composite of the present invention.

To form the pulp board, the fine wettable fibers are placed into a hydropulper with wood pulp fibers and water to form a stock or slurry of between about 1 and about 5% and generally about 2% solids in water. Typically the ratio or percentage of fine wettable fibers to pulp on a dry weight basis will be between about 50% fine wettable fibers/50% pulp (1:1) and 90% fine wettable fibers/10% pulp (9:1) with 70% fine wettable fiber/30% (2.33:1) pulp giving good results.

Once the slurry has been formed, wetting agents, rewetting agents, anti-stats and drainage aids can be added to the slurry usually at a combined addition level of between about 0.1 and 1.0% solids based upon the total solids weight in the slurry. Next the slurry is formed into a board, usually on a fine mesh forming wire, at a weight from about 200 to about 350 pounds per ream (350 and 720 grams per square meter) and a moisture content from about 6 to about 15 percent with 10 to 12 percent by weight working better. If desired, the board can be rolled and compressed for greater uniformity.

Referring to FIG. 1, once the pulp board has been formed it is fed into a fiberizer or defibrator 10 such as a hammermill. Both screen-type and non-screen-type fiberizers can be used, with the non-screen-type exhibiting less plugging. The addition of an anti-stat into the pulp board has been found to help reduce "clinging" of the fibers to the surfaces of the formation equipment as the pulp board is fiberized. Referring again to FIG. 1, as the pulp board 12 is broken up, it is entrained in an air supply which is directed down onto a foraminous forming wire 14. Underneath the forming wire 14 and directly below the fiberizer 10 is a vacuum box 16 which is adjusted to pull a vacuum through the wire 14 of from about 35 to about 60 inches of water (1.5 to 3.0 pounds per square inch) to remove the suspending or entraining air.

As the pulp fibers and fine wettable fibers are directed down onto the forming surface 14, superabsorbent 18 is introduced into duct work 22 positioned below the fiberizer 10. The superabsorbent may be in particle, fiber or flake form. Due to the velocity, volume and turbulence of the entraining air, the pulp fibers, fine wettable fibers and superabsorbent are intimately mixed with one another before they are laid down on the forming surface 14 in the form of a composite web 20. The basis weight of the composite 20 can be tailored to a specific end use but will typically be in the range of about 100 to about 1000 grams per square meter with 300 to 500 grams per square meter usually being the range for such products as diapers and other personal care items.

The basic process as just described can be varied and modified in a number of ways though, generally, it is desirable to use air forming equipment to achieve good mixing of the components. As formed, the composite web 20 may not have sufficient structural integrity. As a result, the composite web 20 may be run through a pair of compaction rollers 24 to further compact and densify the web. Densities will range from about 0.1 to about 0.35 grams per cubic centimeter for personal care product applications. In some applications the composite web 20 may not have sufficient wettability. As a result, additional surfactant may be added to the web via, for example, a sprayer 25. The surfactant may be added to the fibers before the formation of the web 20 as shown in FIG. 1 or it may be sprayed directly onto the formed web (not shown) though this method will generally not ensure application to all the fibers throughout the web.

If still a more structurally intact composite web 20 is desired, binder fibers may be added to the entrained stream of fibers and superabsorbent before formation of the composite web 20 is complete. Referring again to FIG. 1, there is shown an additional fiber source or sources 26 positioned between the fiberizer 10 and the forming wire 14. This fiber source 26 may be adapted to introduce shorter, staple fiber length fibers typically having lengths of 3 to 12 millimeters or longer, more continuous fibers such as are available from meltblowing and spunbond processes. Examples of these processes can be found in U.S. Pat. Nos. 3,849,241; 3,692,618 and 4,340,563 all of which are incorporated herein by reference in their entirety. Generally the binder fibers will be uniformly mixed with the other components and will be present in a weight percent of about 2 to about 8 percent based upon the total weight of the composite web 20. As mentioned previously, suitable binder fibers are those which have a uniform polymer composition across their diameters or they may be non-uniform or even have distinct regions as with bicomponent fibers. The fibers also can have both regular and irregular-shaped cross-sections and they can be either hydrophilic or hydrophobic, though hydrophilic fibers are more desirable for liquid transport.

If thermoplastic or heat fusible fibers are used, a heating source such as hot air or infrared heat may be added to the process to fuse and bond the fibers together. Such a heating source 30 is shown schematically in FIG. 1 just prior to the compaction rollers 24. In operation the heating source 30 heats the fusible fibers to at least their softening point as the compaction rollers compress, bond and densify the composite web 20. The amount of time the web is heated will depend upon the density of the web, the line speed of the web, the amount and softening temperature of the binder and the temperature of the heat being applied. With the materials set forth in the examples, exposure to heated air at a temperature of 140° C. for a period of 15 seconds was sufficient to activate the binder. Depending upon the type of bonder fibers being used, the compaction rollers can be heated and/or cooled or simply operated at ambient temperature. Alternatively, the heating source 30 may be placed downstream, after the compaction rollers (24) to set the fibers after compaction (not shown). In addition, the heating source may be operated without the compaction rollers.

If entrapment of the particulate superabsorbent in the composite web 20 becomes a problem, a material such as tissue paper (not shown) may be placed on top of the forming surface 14 and the composite may be laid down upon the tissue paper which will serve to further trap the superabsorbent particles. Alternatively, separate fiber banks (not shown) may be placed upstream of the present process to form a first layer of fibers on the forming wire 14 prior to the deposition of the materials which form the composite web 20 of the present invention.

Once the composite web has been formed it may remain in-line and be subjected to further processing downstream. Conversely, it may be wound up on a take-up roll 32 and then unwound later for cutting, slitting and further processing.

A second process was also used to create high wicking liquid absorbent composites according to the present invention. The materials of examples 3 through 7 were formed on a rotary screen air former machine at Danwebforming International, Ltd. of Aarhus, Denmark. As with the materials of examples 1 and 2, a pulp board was first formed from wood pulp fibers and fine wettable fibers. This pulp board was then fed into a defibrator. Here the fibers were separated and entrained in an air stream which was fed into a rotary screen air former. At the same time superabsorbent and binder fibers were introduced into the air stream and intimately mixed with the pulp and fine wettable fibers before the mixture was laid down onto a moving forming surface in the form of a composite web. Once the web was formed it was then sent through a pair of compaction rollers before being heated to a temperature high enough to soften and adhere the binder fibers to themselves and the other constituents of the composite. Following bonding, the composite web was cooled and then wound up on winding roll.

Figure 2:
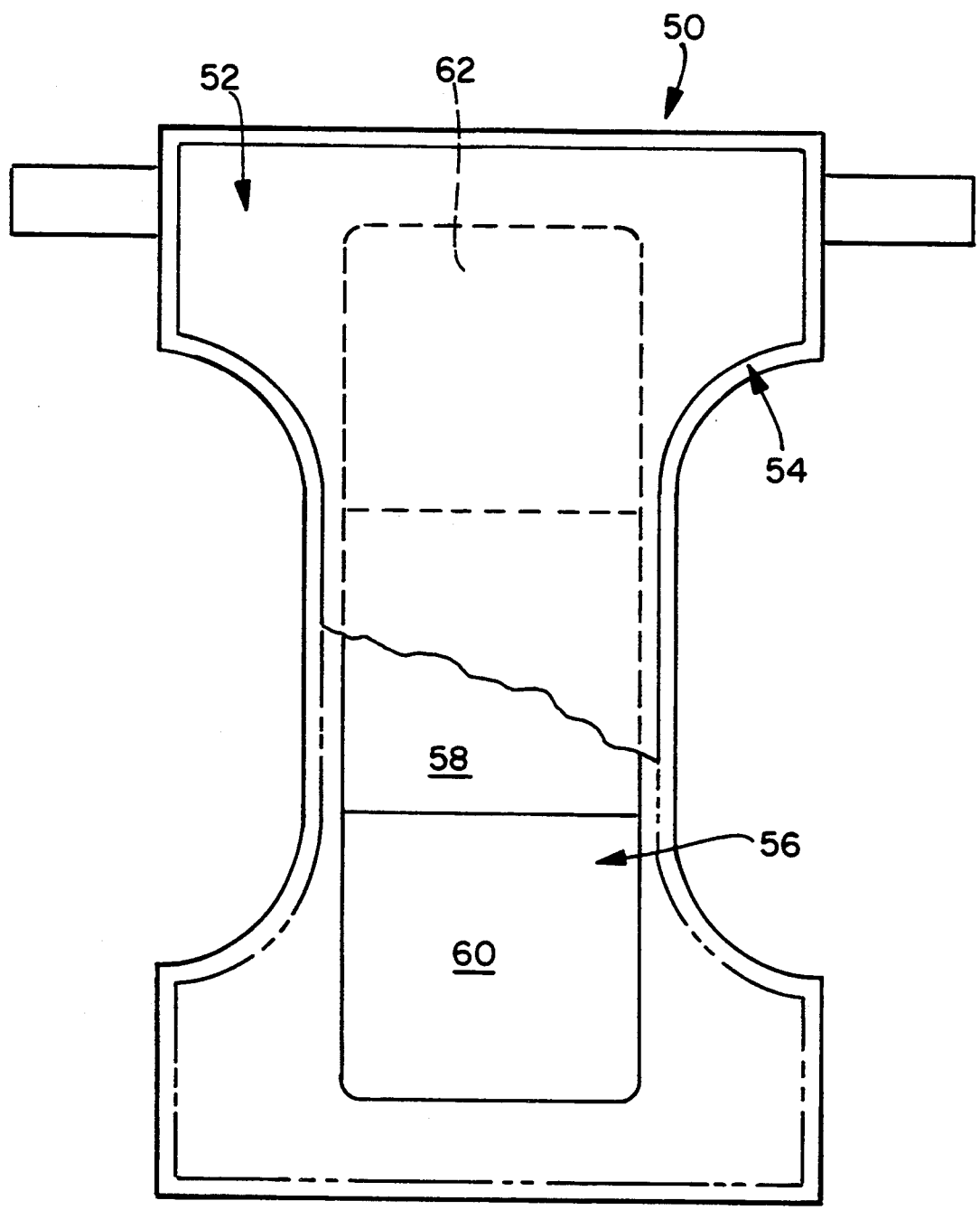
FIG. 2 is a top plan view in partial cut away of a personal care absorbent article including the high wicking liquid absorbent composite according to the present invention.

One use for the material of the present invention is as an absorbent core for personal care products such as diapers, training pants, incontinence garments, sanitary napkins, bandages and the like. An example of such personal care products, a diaper, is shown in FIG. 2. Generally, in a diaper configuration, the composite material of the present invention will have a density of from about 0.1 to about 0.35 grams per cubic centimeter. As with most personal care products, the diaper 50 in its simplest design includes a bodyside liner 52 and an outercover 54 with a liquid-absorbent core 56 disposed therebetween. The purpose of the bodyside liner 52 is to pass liquids and other exudates into the absorbent core 56 where the liquids and other exudates are absorbed, distributed and stored. The purpose of the outercover 54 is to retain the liquids and other exudates and keep them from spreading in unwanted directions.

Testing has shown that while the composite web 20 (absorbent core 56) shows improved wicking characteristics over conventional superabsorbent/fluff composites, it will not always take up liquids such as urine as quickly as conventional absorbents, especially during large insults. As a result, a more refined embodiment of the diaper 50 may include a zoned absorbent core 56. As shown in FIG. 2, the absorbent core 56 has three zones or regions. The central region 58 which occupies roughly the middle third of the diaper 50 is the area in closest proximity to the periheal area of the wearer and thus the area of the wearer from which the body fluids emanate. This material in this area can be a conventional material and therefore substantially devoid of fine wettable fiber. By substantially devoid it is meant that the central region contains less than 5 percent fine wettable fiber based upon the total weight of the material in this region.

Conversely, the forward region 60 and the rearward region 62, which collectively occupy the remaining roughly two thirds of the absorbent core 56 on opposed sides of the central region 58, are comprised of the high wicking liquid-absorbent composite web according to the present invention. As a result, when liquid insults the central region 58 of the absorbent core 56, the liquid is rapidly taken up. Once the liquid is taken up, the forward 60 and rearward 62 regions of the absorbent core 56 can wick the liquids away to the regions of the diaper 50 adjacent the waist of the wearer thereby increasing the overall capacity of the diaper 50. Given the increased utility of the diaper 50, it is in turn possible to reduce the amounts of material placed in the diaper thereby permitting thinner, more efficient diaper constructions. As will be readily appreciated from the foregoing, it is possible to shift the relative positions of the regions 58, 60 and 62. For example, in male-specific diaper designs the central region 58 may be moved up more toward the front of the diaper to more properly coincide with the male anatomy. In addition, the size and shape of the regions may be varied and the location and number of regions may be altered.

Vertical Wicking Test

To test the liquid transport properties of the present invention and other materials, a vertical wicking test was performed to determine how high during a one hour period a liquid could be wicked up a sample of material one end of which had been placed in a constant volume reservoir of synthetic urine.

Samples of the material were cut into 4 inch by 15 inch pieces. Each piece was then wrapped around the bottom end and two sides of a piece of acrylic board measuring 9 and 3/16 inches high by 5 inches wide by ¼ inch thick such that the 4 inch wide ends of the sample extended equally up both sides of the height of the acrylic board (approximately 7 ½ inches). The samples were held in place on the board by two clamps extended around the side edges of the board so as to grasp the side edges of the sample near the top of the sample. The side of the board was scaled in 1 mm increments to measure the vertical height of the wicked liquid.

Once the sample had been prepared it was hung from a free swinging support clamp and the sample was then lowered until the lower folded edge of the sample was contacting the reservoir of test liquid. A timer with one second increments was started just as the sample was lowered into the liquid. As the liquid wicked up the sample material, the vertical position of the liquid front relative to the constant level liquid surface was monitored as a function of time. The vertical height of the liquid at the end of one hour was recorded as an indication of the wicking height and thus the capillary drawing power of the sample material.

A synthetic urine solution using the compounds set forth in Table 1 below was used as the wicking medium in the vertical wicking test. To formulate the test solution, 900 milliliters of distilled water was added to a 1000 milliliter volumetric flask. The compounds were added in the order given in Table 1 to avoid precipitating divalent cations due to the high pH of the solution. Each compound was completely dissolved before adding the next compound. Once all the compounds had been added, the flask was brought to a volume of 1000 milliliters.

TABLE 1

| Compound | Concentration g/l |
| --- | --- |
| $KH_2PO_4$ F.W. = 136 | 0.681 |
| $Ca(H_2PO_4)_2\ H_2O$ F.W. = 252.1 | 0.309 |
| $MgSO_4\ 7H_2O$ F.W. = 246.5 | 0.477 |
| $K_2SO_4$ F.W. = 174.3 | 1.333 |
| $Na_3PO_4\ 12H_2O$ F.W. = 380.2 | 1.244 |
| NaCl F.W. = 58.4 | 4.441 |
| KCl F.W. = 74.5 | 3.161 |
| $NaN_3$ F.W. = 65.0 | 0.400 |
| Urea ($NH_2CONH_2$) F.W. = 60.1 | 8.560 |
| Pluronic 10R8* F.W. = 5000 | 0.100 |

*a wetting agent manufactured by BASF Corporation of Parsippany, New York.

With each batch of test liquid, a few drops of colored dye was added to improve visual observation of the liquid as it wicked up the test samples.

EXAMPLES

EXAMPLE 1

A high wicking material according to the present invention was formed via a formation process similar to that shown in FIG. 1. The material included 62% by weight IM5000P superabsorbent granules produced by Hoechst Celanese Corporation of Richmond, Va., 16% by weight CR2054 fluffing pulp produced by Kimberly-Clark Corporation of Neenab, Wis. and 16% by weight cellulose acetate Fibrets ® fibers produced by Hoechst Celanese Corporation of Charlotte, N.C. The high wicking material also included 6% by weight generally continuous macroscopic meltblown polypropylene reinforcing fibers having average diameters of approximately 15 microns. The polypropylene for the fibers was obtained from Himont Polymers of Norcross, Ga. and prior to extrusion of the fibers, there was incorporated into the polypropylene resin 2% by weight, based upon the total weight of the polypropylene fiber, Mapeg 400 DO additive, a surface wettability enhancer produced by PPG Mazer Chemical Corporation of Pittsburgh, Pa. This additive contained 400 molecular weight polyethyleneglycol di-oleate ester. The foregoing pulp fibers, superabsorbent, fine wettable fibers and reinforcing fibers were uniformly mixed with one another and then laid down on a forming wire to form a high wicking absorbent web according to the present invention. No bonding or compression of the web was undertaken. The web had a basis weight of approximately 400 grams per square meter (gsm) and a density of about 0.2 grams per cubic centimeter (g/cc). The Mapeg 400 DO additive increased the wetting of the polypropylene reinforcing fibers which in turn were used to increase the integrity of the overall structure. The sample was heated for 30 seconds at 80° C. to "activate" the wetting system in the polypropylene. As can be seen from Table 2, the vertical wicking height of the sample over a 60 minute period was 13 centimeters.

TABLE 2

| SAMPLE | VERTICAL WICKING HEIGHT |
|---|---|
| 1 | 13 cm |
| 2 | 10 cm |
| 3a (control) | 11 cm |
| 3b | 14 cm |
| 4a (control) | 5 cm |
| 4b | 10.5 cm |
| 5a (control) | 9 cm |
| 5b | 13 cm |
| 6a (control) | 9 cm |
| 6b | 14 cm |
| 7a (control) | 7 cm |
| 7b | 11 cm |

EXAMPLE 2

In Example 2, a material was formed in accordance with a process similar to that shown in FIG. 1. The material used the same components as Example 1, the difference being the relative weight percent of each component. The material in Example 2 comprised 80% by weight superabsorbent, 3% by weight fluffing pulp, 14% by weight cellulose acetate fibrets ® fine wettable fibers and 3% by weight polypropylene reinforcing fibers. The material had a basis weight of 375 grams per square meter and a density of about 0.2 grams per cc. As can be seen from Table 2, this material had a vertical wicking height over a 60 minute period of 10 centimeters which was less than the value for Example 1. While not wishing to be bound by the present hypothesis, it is believed that the decrease in vertical wicking height was due to the reduction in the amount of cellulose acetate fine wettable fibers and the reduced ratio between the amount of fine wettable fibers as compared to the amount of superabsorbent.

EXAMPLE 3

In Example 3, two sample materials (Samples 3a and were made. Samples 3a was in essence a control as it did not contain any fine wettable fibers while sample 3b did contain fine wettable fibers. Both samples in Example 3 were made at Danwebforming International, Ltd. of Aarhus, Denmark in accordance with the process described above.

The sample 3a material included 75% by weight of an experimental high liquid retention/high gel strength superabsorbent produced by Dow Chemical Corporation of Midland, Mich., 19% by weight CR2054 fluffing pulp produced by Kimberly-Clark Corporation of Neenah, Wis. and 6% by weight Danaklon ES-C bicomponent polyolefin binder fibers from Danaklon a/s of Varde, Denmark. The binder fibers were 3.3 decitex (dtex) fibers with a length of 6 mm. Prior to incorporation of the pulp and binder fibers into the air forming mixture, the pulp and binder fibers were formed into a premix which was formed into a pulp board which was then refiberized using a small hammermill. The pulp and binder fibers were then mixed with the superabsorbent in an air forming process to form a composite web having a basis weight of about 400 gsm and a density of about 0.2 g/cc. The bicomponent binder fibers were used to fuse the web and increase its integrity. The bonding of the binder fibers was accomplished by heating the sample web in a through-air oven at a temperature of approximately 140° C. for approximately 15 seconds. Sample 3a (control) had a vertical wicking height of 11.0 cm over a 60 minute period.

Sample 3b was also made using the same process and components as sample 3a with the addition of cellulose acetate Fibrets ® fibers, a fine wettable fiber. Sample 3b included 75% by weight superabsorbent, 14% by weight cellulose acetate fibrets ® fine wettable fibers, 6% by weight fluffing pulp and 5% by weight bicomponent polyolefin binder fibers. As with example 3a, the pulp, fine wettable fibers and binder fibers were premixed and formed into a pulp board which was then refiberized and introduced into the air forming process to form a composite having a basis weight of about 400 grams per square meter and a density of about 0.2 grams per cc with the binder fiber being fused at a temperature of about 140° C. in a through-air oven. Sample 3b had a vertical wicking height of 14.0 cm over a 60 minute period. This was an increase in vertical wicking height of over 27 percent when compared to the 11.0 cm vertical wicking height of the control, Sample 3a.

EXAMPLE 4

In Example 4, two samples were prepared with sample 4a being the control and 4b being the sample made according to the present invention. As with Samples 3a and 3b, both of these samples were made using an air forming system at Danwebforming International, Ltd. of Aarhus, Denmark. Sample 4a comprised 70% by weight of a developmental acrylate superabsorbent 10 decitex by 6 mm fiber labeled "FSA ® 101" produced by a joint venture of Courtaids Fibers Ltd. of Coventry, UK and Allied Colloids, Ltd. of Bradford, UK, 23% by weight Weyerhauser NB-416 fluffing pulp produced by Weyerhauser Corporation of Federal Way, Washington and 7% by weight Danaklon bicomponent polyolefin binder fiber of the same type mentioned in the previous examples. The finished composite had a basis weight of about 400 gsm and a density of about 0.2 grams per cc. The material was fused at a temperature of approximately 140° C. in a through-air oven and had a vertical wicking height of 5 cm over a 60 minute period.

Sample 4b used 75% by weight of the same superabsorbent fiber as sample 4a. Intimately mixed with the superabsorbent fibers in the air forming process was 13% by weight of the cellulosic acetate Fibrets ® fine wettable fibers, 5% by weight of the fluffing pulp and 7% by weight of the Danaklon PE/PP eccentric sheath core fiber. The fine wettable fibers, pulp and bicomponents fibers were the same as those previously mentioned in the preceding examples. The composite web was passed through a through-air oven at a temperature of approximately 140° C. to melt the sheaths of the bicomponent fibers to form a more structurally intact web according to the present invention. The finished composite web had a basis weight of approximately 400 grams per square meter and a density of about 0.2 grams per cc. The vertical wicking height of this material over a 60 minute period was 10.5 centimeters which represented a 110 percent increase in vertical wicking capability for the material of the present invention (sample 4b) as compared to the control (Sample 4a).

EXAMPLE 5

In Example 5, two samples 5a and 5b were prepared with 5a being the control which did not contain any fine wettable fibers. Both samples 5a and 5b were formed using the same forming process as in Example 3. Sample 5a comprised 75% by weight of the same developmental acrylate superabosrbent 10 decitex by 6mm FSA ® 101 fiber from Example 4, 20% by weight NB416 fluffing pulp produced by Weyerhauser Corporation of Federal Way, Washington and 5% by weight of the bicomponent PE/PP binder fiber mentioned in the previous examples and produced by Danaklon a/s of Varde, Denmark. The finished composite had a basis weight of about 400 grams per square meter and a density of about 0.2 grams per cc. The material once formed was fused by heating the sample to a temperature of approximately 140° C. in a through-air oven to fuse and bind the bicomponent fibers. Sample 5a had a vertical wicking height of 9 centimeters over a 60 minute period.

Sample 5b used the same superabsorbent fibers and bicomponent fibers as sample 5a and the same cellulose acetate fine wettable fibers and fluffing pulp as used in sample 4b. Sample 5b contained 75% by weight superabsorbent fiber, 16% by weight cellulose acetate fibrets ® fine wettable fibers, 4% by weight fluffing pulp and 5% by weight bicomponent polyolefin binder fiber. The finished sample had a basis weight of approximately 400 grams per square meter and a density of about 0.2 grams per cc. As with sample 5a, sample 5b was fused at a temperature of about 140° C. in a through-air oven and had a vertical wicking height of 13 centimeters over a 60 minute period. This represented a 44 percent increase in vertical wicking capability as compared to the control (sample 5a).

EXAMPLE 6

In Example 6, there were two samples (6a and 6b) with sample 6a being the control which did not contain any fine wettable fiber. Sample 6a used the same components as sample 5a except for the length of the superabsorbent fiber which was 12 mm instead of 6 mm. The sample comprised 75% by weight superabsorbent fiber, 20% by weight fluffing pulp and 5% by weight of bicomponent PE/PP binder fiber. Sample 6a and 6b were formed using the same process described with respect to Example 3. Sample 6a had a basis weight of about 400 grams per square meter and a density of 0.2 grams per cc with the binder fibers having been fused at a temperature of about 140° C. in a through-air oven. Control sample 6a had a vertical wicking height of 9 centimeters over a 60 minute period.

Sample 6b used the same materials as did sample 5b. Sample 6b comprised 75% by weight superabsorbent fiber, 16% by weight fine wettable fiber, 4% by weight fluffing pulp and 5% by weight bicomponent binder fiber. As with the other samples, the finished composite had a basis weight of about 400 gsm and a density of 0.2 grams per cc with the binder fibers being fused at a temperature of about 140° C. in a through-air oven. Sample 6b according to the present invention had a vertical wicking height of 14 centimeters over a 60 minute period. This represented a 56 percent increase in vertical wicking capability as compared to the control (Sample 6a).

EXAMPLE 7

In Example 7, two samples were prepared, samples 7a and 7b with sample 7a serving as the control as it contained no fine wettable fiber. Both samples were made using the process described with respect to Example 3. Sample 7a comprised 75% by weight of a developmental acrylate superabsorbent 10 dtex by 12 mm fiber labeled "FSA ® 111" produced by a joint venture of Courtaids Fibers Ltd. of Coventry, UK and Allied Colloids, Ltd. of Bradford, Uk, 20% by weight CR2054 fluffing pulp from Kimberly-Clark Corporation of Neenah, Wis. and 5% by weight bicomponent polyolefin binder fiber (Danaklon ES-C 3.3 dtex by 6 mm fibers from Danakalon a/s of Varde, Denmark). The material had a vertical wicking height of 7.0 cm over a one hour period.

Sample 7b used the same materials as sample 7a with the addition of the cellulose acetate fine wettable fibers described and used in sample 6b. Sample 7b comprised 75% by weight superabsorbent fiber, 16% by weight fine wettable fiber, 4% fluffing pulp and 5% by weight binder fiber. The finished composite was fused at a temperature of about 140° C. in a through air oven and had a density of about 0.2 g/cc and a basis weight of about 400 grams per square meter. The vertical wicking height of the material was 11.0 cm in a one hour period. This represented a 57% increase in vertical wicking height as compared to the control sample.

With all the foregoing examples it can be seen that dramatic increases in wicking ability can be achieved through the addition of fine wettable fiber into the absorbent structure of the present invention to aid in liquid distribution when high loadings of superabsorbent are used. By using the fine wettable fiber, capillarity within the absorbent structure is improved so that liquids can be transported away from the insult zone to more remote areas thereby increasing the overall capacity and thus the utility of the absorbent structure.

Having thus described the invention in detail, it should be apparent that various modifications and changes can be made in the present invention without departing from the spirit and scope of the following claims.

We claim:

1. A high wicking liquid absorbent composite comprising:
a relatively uniform mixture of from about 5 to about 20 percent fine wettable fiber having a length less than about 2 millimeters and a fiber diameter between about 0.5 and 5.0 microns, from about 3 to about 30 percent pulp fibers, from about 50 to about 90 percent superabsorbent and from 0 to about 10 percent binder, said percentages being on a dry weight basis, based upon the total weight of said mixture, said mixture being compressed into a composite having a density of from about 0.1 to about 0.5 grams per cubic centimeter and, a vertical wicking height of at least about 10 centimeters in one hour.

2. The composite of claim 1 wherein said fine wettable fiber has a fiber diameter of between about 0.5 and about 2.0 micrometers.

3. The composite of claim 1 wherein said superabsorbent is in fiber form.

4. The composite of claim 1 wherein said superabsorbent is in the form of flakes.

5. The composite of claim 1 wherein said superabsorbent has a liquid retention capacity of at least about 10 grams per gram in 0.9% saline solution under a load of 3500 pascals.

6. The composite of claim 1 wherein said composite has a first area and a second area, said second area having a greater amount of fine wettable fiber on a dry weight basis than said first area.

7. The composite of claim 2 wherein said fine wettable fiber has an advancing contact angle less than 90 degrees.

8. The composite of claim 2 wherein said fine wettable fiber has an advancing contact angle less than 70 degrees.

9. An absorbent article comprising:
a liquid pervious top sheet and a liquid impervious backing sheet with a liquid absorbent core disposed therebetween, said core comprising a relatively uniform mixture of from about 5 to about 20 percent fine wettable fiber having a length less than about 2 millimeters and a fiber diameter between about 0.5 and 5.0 microns, from about 3 to about 30 percent pulp, from about 50 to about 90 percent superabsorbent and from 0 to about 10 percent binder, said percentages being on a dry weight basis, said mixture being compressed into a composite having a density of from about 0.1 to about 0.35 grams per cubic centimeter and, said composite having a vertical wicking height of at least about 10 centimeters per one hour.

10. The personal care absorbent article of claim 9 wherein said article is in the form of a diaper.

11. The personal care absorbent article of claim 9 wherein said article is in the form of a training pant.

12. The personal care absorbent article of claim 9 wherein said article is in the form of an incontinence garment.

13. The personal care absorbent article of claim 9 wherein said article is in the form of a sanitary napkin.

14. The personal care absorbent article of claim 9 wherein said article is in the form of a bandage.

15. The personal care absorbent article of claim 9 wherein said core has a first area and a second area, said second area having a greater amount of said fine wettable fiber than said first area.

* * * * *

UNITED STATES PATENT AND TRADEMARK OFFICE
CERTIFICATE OF CORRECTION

PATENT NO. : 5350370

DATED : September 27,1994

INVENTOR(S) : David M. Jackson, Billie J. Matthews

It is certified that error appears in the above-identified patent and that said Letters Patent is hereby corrected as shown below:

Column 9, line 37, "periheal" should read --perineal--;

Column 11, line 10, "Neenab, Wis." should read --Neenah, Wis.--;

Column 12, line 9, "3a and were" should read --3a and 3b) were--;

Column 12, line 68, "Courtaids" should read --Courtalds--;

Column 14, line 41, "Courtaids" should read --Courtalds--.

Signed and Sealed this

Third Day of October, 1995

Attest:

BRUCE LEHMAN

Attesting Officer

Commissioner of Patents and Trademarks